(12) United States Patent
Rotman

(10) Patent No.: US 6,596,496 B1
(45) Date of Patent: *Jul. 22, 2003

(54) ANALYTICAL SYSTEM BASED UPON SPORE GERMINATION

(76) Inventor: M. Boris Rotman, 1062 E. Shore Rd., Jamestown, RI (US) 02835

( * ) Notice: Subject to any disclaimer, the term of this patent is extended or adjusted under 35 U.S.C. 154(b) by 0 days.

This patent is subject to a terminal disclaimer.

(21) Appl. No.: 09/441,531

(22) Filed: Nov. 16, 1999

Related U.S. Application Data

(63) Continuation-in-part of application No. 09/193,385, filed on Nov. 17, 1998, now Pat. No. 6,228,574.
(60) Provisional application No. 60/134,781, filed on May 19, 1999.

(51) Int. Cl.[7] ................ G01N 33/53; G01N 33/567; G01N 35/569
(52) U.S. Cl. ................ 435/7.1; 435/7.2; 435/7.22; 435/7.91
(58) Field of Search ............... 435/6, 7.2, 7.22, 435/7.31, 7.5, 7.32, 7.71, 7.91, 25, 29

(56) References Cited

U.S. PATENT DOCUMENTS

| | | | | |
|---|---|---|---|---|
| 5,418,167 A | * | 5/1995 | Matner et al. | 435/288 |
| 5,472,846 A | * | 12/1995 | Rotman | 435/7.23 |
| 5,614,375 A | * | 3/1997 | Citri | 435/29 |

* cited by examiner

Primary Examiner—James Housel
Assistant Examiner—Zachariah Lucas
(74) Attorney, Agent, or Firm—Bruce Jacobs

(57) ABSTRACT

An analytical system for rapid detection and identification of different analytes directly from a test sample by mixing test material with a germinogenic source and enzyme-free spores, allowing the mixture to stand for a time to allow analyte-induced spore germination and subsequent de novo activity of an enzyme capable of producing a germinant in the presence of the germinogenic source and detecting the presence of a germination-derived product. The germinant which is formed promotes further spore germination with concomitant additional de novo enzyme synthesis or activation which results in a propagating cascade of analyte-independent germination after which a germination-derived product can be easily detected. The technique is particularly efficient to conduct thousands of parallel assays in an array of microscopic wells.

11 Claims, 1 Drawing Sheet

ANALYTICAL SYSTEM BASED UPON SPORE GERMINATION

This application claims the benefit of U.S. Provisional Application No. 60/134,781 May 19, 1999.

This application is a continuation-in-part of application Ser. No. 09/193,385 filed on Nov. 17, 1998 now U.S. Pat. No. 6,228,574.

TECHNICAL FIELD

This invention is in the fields of biological and biochemical assays. Most particularly, it relates to novel assays for microorganisms, viruses, nucleic acids, and polypeptides.

BACKGROUND OF THE INVENTION

In various areas of medical diagnostics there is an urgent need for new technology capable of reducing time and cost of existing analytical tools. For example, standard diagnostic tests for infectious disease are not sufficiently rapid for early diagnosis of sepsis, a life-threatening systemic disease affecting each year approximately 400,000 individuals in the U.S. alone. In most patients, septic shock occurs when gram-negative bacteria enter the blood stream following local bacterial infections such as meningitis, pneumonia, and urinary tract infections. Clinical data indicate that early diagnosis of sepsis is crucial because the risk of death increases substantially when treatment is delayed.

Standard bacteriological tests need 24–48 hours for completion because they require a preliminary amplification/purification step in which a specimen is first cultured in agar until visible bacterial colonies appear. Subsequently, one or more of the bacterial colonies is collected and tested for antibiotic resistance and/or bacterial identification markers.

Progress in the last two decades in this field has been mainly limited to improving the process of colony testing using automated analyzers based on chromogenic and fluorogenic enzymatic reactions. The currently available analyzers, however, still require about one fourth of a bacterial colony (about $2\times10^7$ cells) for each biochemical test, and bacterial identification takes 3–12 hours.

The BCR-methodology disclosed in U.S. Pat. No. 5,472,846 and the amplification system of the present invention are radically different methodologies although both make use of living microorganisms for amplification. In contrast to BCR: (1) the present invention does not require growth of vegetative bacterial cells since it depends exclusively on spore germination; (2) this invention does not require enzyme-labeled probes; (3) the chain reaction in this invention consists of a propagating cascade of spore germination generated through de novo synthesized or activated enzymes acting on a germinogenic source present in the reaction mixture whereas the chain reaction in BCR consists of bacterial proliferation generated through enzymatic destruction of a growth inhibitor, typically an antibiotic, present in the reaction mixture; and (4) this invention requires spores and cannot operate with vegetative cells, while BCR can operate equally well with spores or vegetative cells.

Another methodology which makes use of bacterial spores is disclosed by N. Citri in U.S. Pat. No. 5,614,375. Citri teaches detection of biotoxic contaminants based upon their inhibitory effect on enzyme synthesis which occurs de novo during spore germination. The differences between Citri and the present invention become clear when testing bacteria or other particulate analytes since Citri's methodology is not capable of either detecting or identifying these types of analytes whereas the present invention does so.

Accordingly, it is an object of the present invention to provide an improved biological/biochemical assay for determining the presence of various microorganisms, viruses, nucleic acids, and polypeptides in a test sample.

SUMMARY OF THE INVENTION

The present invention provides an exponential signal-amplification method for detecting an analyte which entails the steps of: (1) contacting a sample containing a suspected analyte with a reaction mixture comprising (i) microbial spores that sense an analyte-specific signal and respond to the signal by establishing an analyte-independent signal amplification system and (ii) a germinogenic source; (2) incubating said mixture for a time sufficient to allow for catalytic conversion of the germinogenic source to a germinant, and for spore germination; and (3) detecting spore germination by a measurable parameter.

The present invention also provides apparatus and kits for assaying a variety of analytes using this method to amplify analyte-specific biochemical signals.

This invention uses microbial spores to integrate signal-sensing, signal-amplification, and readable outputs. In the presence of an analyte and a germinogenic source, this invention provides a propagating cascade of analyte-independent amplification reactions driven by spore germination. The end point of the reactions is massive spore germination which can be measured using any of several standard methods.

The invention further provides different embodiments for a novel biosensor for detecting and identifying analytes consisting of particulate, discrete entities. While some of these analytes are naturally present as discrete particles (e.g. microbial cells, viruses, and mammalian cells present in body fluids), others may be specifically attached to beads or other particles prior to analysis in the biosensor. A notable feature of the biosensor is that it provides for thousands of parallel analyses which can be simultaneously quantified using computerized imaging equipment.

BRIEF DESCRIPTION OF THE DRAWINGS

FIG. 1 includes a top view and two cross-sectional views of portions of the biosensor.

DESCRIPTION OF THE PREFERED EMBODIMENTS

Figure 1:
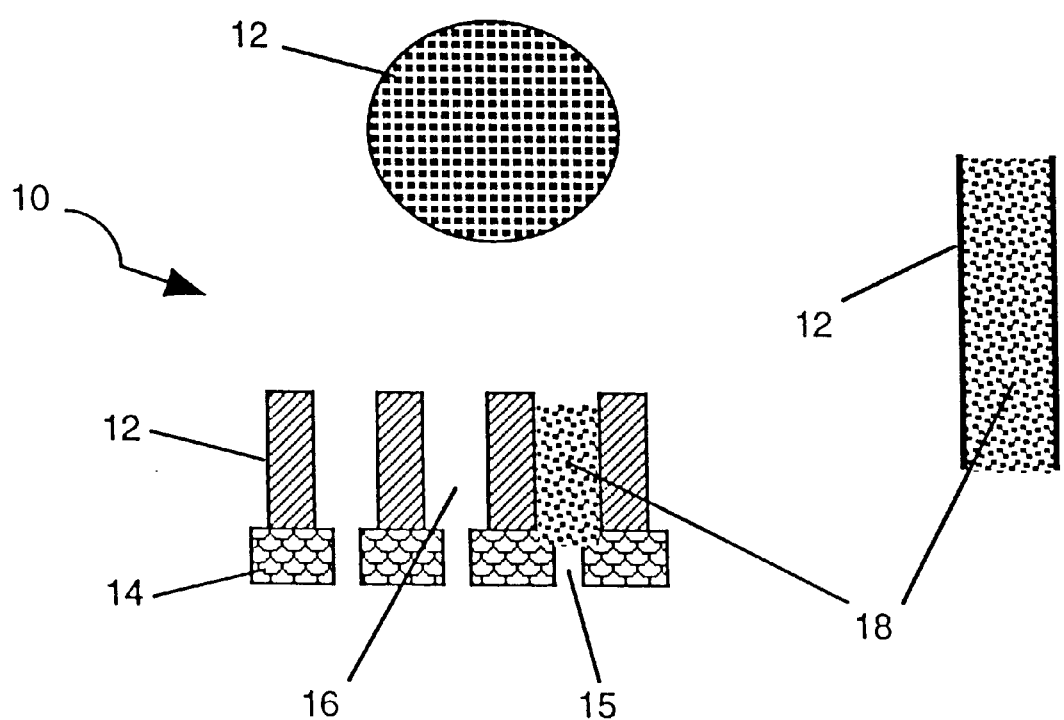
FIG. 1 is a diagramatical view of a biosensor used in an embodiment of the present invention.

The present invention provides methods of, apparatus for, and test kits for the detection and identification of target cells, molecules, and other analytes through the use of living microbial spores that sense analyte-specific signals and respond to them by establishing an analyte-independent signal amplification system. The invention provides a system which permits the rapid detection and identification of different analytes including microorganisms, viruses, nucleic acids and polypeptides.

More particularly, the method entails the steps of:

(1) contacting a sample containing a suspected analyte with a reaction mixture of microbial spores (either as present in nature or genetically-modified) and a "germinogenic" source. A "germinogenic" source is a material which indirectly induces spore germination, i.e., one or more molecules which upon the presence of an enzyme generates a germinant, i.e., an inducer of spore germination. The term "germinogenic" is used herein similarly to the terms "chromogenic" and "fluorogenic" when describing enzyme substrates. The germinogenic source must not be a germinant for the spores in the reaction mixture.

(2) incubating the mixture for a time sufficient to allow for enzymatic conversion of the germinogenic source into a germinant and for spore germination due to the newly formed germinant; and then (3) detecting spore germination by some measurable parameter, such as loss of spore birefringence or appearance of de novo enzymatic activity, e.g. due to enzyme(s) activation or synthesis in the germinating spores.

The invention operates through direct biochemical interactions between an analyte and microbial spores acting as multifunctional nanodevices. The spores may be either as found in nature or genetically-modified to produce certain enzymes during spore germination. The invention utilizes inherent biological mechanisms which allow spores to sense specific germination signals and transduce them into signals promoting extensive de novo enzymatic activity.

There are a great number of bacterial species which produce spores that are suitable for use in the invention. For example, the following members of the genus Bacillus (widely dispersed in soil, plant matter, and air) may be readily grown in the laboratory to form spores: *B. cereus, B. licheniformis, B. megaterium, B. sphaericus, B. sterarothermophilus, B. subtilis,* and *B. thuringiensis.* Another example of a suitable bacterial species is the genus Clostridium, e.g. *C. mucosum, C. butyricum,* and *C. alcaligenes.*

Alternatively, spores from yeasts, molds, and other fungi are also suitable for use in the present invention. Examples of such microorganisms include, but are not limited to, *Dictyostelium discoideum, Neurospora crassa, Saccharomyces cerevisiae, Saccharomyces chevalieri,* and *Saccharomyces ellipsoideus.* Alternatively, spores from plants may be used.

Suitable germinogenic sources comprise molecules which are capable of producing a germinant molecule when subjected to an appropriate catalytic, preferably enzymatic, reaction or reactions. Examples of suitable "simple" germinogenic sources include L-alanine-p-nitroanilide, L-pyroglutamyl-L-alanine, benzoyl-L-arginyl-L-alanine, N-tosyl-glycyl-1-propyl-L-arginyl-L-alanine, L-alanyl-ethanol, adenosine 3'-monophosphate, adenosine-β-D-galactopyrano-side, adenosine-β-D-glucuronide, L-alanine-cephalosporin, and adenosine-cephalosporin. These molecules when contacted by an appropriate enzyme will directly form a germinant, i.e., a compound which will cause spore germination to occur.

In certain instances, a spore may require the presence of two or more compounds before germination will occur. In this case, a suitable germinogenic source will need to include a mixture of molecules which will generate multiple germinants. Spores of *B. cereus,* for example, require exposure to both adenosine and L-alanine for germination.

In other instances, a complex germinogenic source may be used. In this case an enzyme generates a reaction product which in turn is converted into a germinant in the presence of one or more additional molecules. Suitable complex germinogenic sources allow for the identification of specific analytes and thus are generally highly specific. Some detailed examples of complex germinogenic sources include but are not limited to:

1. A mixture of L-tryptophan, L-glutamic acid, and glutamic-pyruvic transaminase (EC 2.6.1.2), an enzyme catalyzing formation of L-alanine from pyruvic and L-glutamic acids. This germinogenic source results in the production of the germinant L-alanine in the presence of an analyte endowed with tryptophanase activity. This occurs when the presence of tryptophanase converts the L-tryptophan in the source into pyruvic acid which, in turn, is converted to L-alanine (the germinant) in the presence of glutamic acid and the enzyme glutamic-pyruvic transaminase.

2. A mixture of adenosine diphosphate (ADP), L-glutamine, orthophosphate, pyruvic acid, and glutamic-pyruvic transaminase (EC 2.6.1.2). This germinogenic source produces the germinant L-alanine in the presence of an analyte endowed with glutamine synthase (EC 6.3.1.2) activity. This occurs due to glutamine synthase formation of L-glutamic acid in the presence of ADP, L-glutamine and orthophosphate. In turn, L-glutamic acid and pyruvic acid are converted into L-alanine by the glutamic-pyruvic transaminase in the source.

3. A mixture of D-glutamic acid, pyruvic acid, and glutamic-pyruvic transaminase (EC 2.6.1.2). This germinogenic source produces the germinant L-alanine in the presence of an analyte endowed with glutamate racemase (EC 5.1.1.3) activity. The reason is that glutamate racemase converts D-glutamic acid into L-glutamic acid which in the presence of pyruvic acid and glutamic-pyruvic transaminase (EC 2.6.1.2) generates L-alanine.

Examples of germinants which can be derived from a germinogenic source include, but are not limited to, adenosine, L-alanine, L-asparagine, D-fructose, D-glucose, inosine, L-proline, L-valine, L-leucine, L-glutamine, L-threonine, and D-ribose.

As used herein, "de novo enzyme activity" refers to the appearance of enzymatic activity that occurs exclusively after germination of spores which are basically devoid of detectable enzymatic activity. The spores are from bacterial strains specifically selected to produce de novo enzyme activity capable of generating an analyte-independent cascade reaction in the presence of a germinogenic source. Table II below identifies examples of this type of enzyme and corresponding germinogenic substrates.

As used herein, "analyte-independent cascade reactions" comprise enzymatic reactions in which de novo enzyme activity and its corresponding germinogenic source produce a self-sustained cycle of four sequential events: (1) induction of spore germination; (2) de novo enzyme activity by the germinating spore; (3) de novo production of germinant molecules from a germinogenic source; and (4) further induction of spore germination.

Table I lists several spore-forming bacteria and corresponding germinants. Spore-forming bacteria in which the specificity of the germinant has been altered, e.g. by chemical treatment or mutation, may also be used herein.

TABLE I

Spore Forming Bacteria and Corresponding Germinant

| Bacteria | Germinant |
|---|---|
| Bacillus cereus | Adenosine and L-alanine |
| Bacillus licheniformis | Glucose and Inosine |
| Bacillus megaterium | Glucose, L-proline, and KBr |
| Bacillus subtilis | L-alanine |

It is an important feature of this invention that the combination of spore, germinogenic source, and enzyme, has the capability of promoting an analyte-independent cascade reaction resulting in massive spore germination.

Thus the germinogenic enzyme synthesized de novo or activated during spore germination must be capable of using the germinogenic source present in the assay to directly or indirectly produce a germinant.

The inventive method can employ many germinogenic source—enzyme combinations. Examples of some enzymes and corresponding suitable germinogenic sources are listed in Table II.

TABLE II

Enzymes and Suitable Corresponding Germinogenic Sources

| Enzyme | Germinogenic Source |
| --- | --- |
| L-alanine aminopeptidase | L-alanine-p-nitroanilide |
| Pyroglutamyl aminopeptidase | L-pyroglutamyl-L-alanine |
| Proteases | Benzoyl-L-arginyl-L-alanine |
| Coagulase | N-tosyl-glycyl-1-propyl-L-arginyl-L-alanine |
| Esterases | L-alanyl-ethanol |
| Phosphatases | Adenosine 3'-monophosphate |
| β-D-Galactosidase | Adenosine-β-D-galactopyranoside |
| β-D-Glucuronidase | Adenosine-β-D-glucuronide |
| β-Lactamase II | L-alanine-cephalosporin |
| β-Lactamase II | Adenosine-cephalosporin |

The present invention is designed to detect the presence, and in some cases the quantity of specific target analytes. As used herein the term "analyte" is meant to refer to a variety of targets to be detected including (i) microbes such as bacteria, fungi, and protozoa, as well as (ii) viruses, (iii) nucleic acid macromolecules, and (iv) naturally soluble macromolecules which have been immobilized in or on discrete particles. The target analyte must be capable of, or made capable of at some point during analysis, generating a germinant by enzymatic (catalytic) action on a germinogenic source.

Illustrative examples of useful analytes include, but are not limited to, the following: (1) microorganisms which contain germinogenic enzymes (enzymes which will cause spore germination), or which contain enzymes capable of becoming germinogenic when combined with another enzyme(s); (2) eukaryotic or prokaryotic organisms with cell-surface macromolecules and antigens (including cytokines, hormones, protein complexes, and molecules recognized by cell receptors) capable of being specifically tagged with a germinogenic enzyme; (3) cellular or viral proteins, DNA or RNA specifically tagged with a germinogenic enzyme; and (4) soluble macromolecules. Detection of such analytes is particularly useful in clinical situations where rapid detection of an analyte is important for therapy.

Examples of suitable bacteria for detection in accordance with the present invention include: *Enterobacter aerogenes, Escherichia coli, Chlamydia trachomatis, Clostridium botulinum, Clostridium tetani, Haemophilus influenza, Klebsiella pneumoniae, Neisseria gonorrhoeae, Proteus mirabilis, Salmonella typhimurium, Serratia marcenses, Shigella sonnei, Staphylococcus aureus,* and *Streptococcus pyogenes.*

Examples of suitable fungi and protozoa for detection include: *Aspergillus fumigatus, Blastomyces dermatitidis, Candida albicans, Cryptococcus neoformans,* and *Trichomonas vaginalis.*

Examples of suitable viruses for detection include: cytomegalovirus, hepatitis viruses, herpes viruses, and human immunodeficiency viruses.

Examples of suitable nucleic acid macromolecules include: DNA and RNA from bacteria, viruses and other infectious agents; DNA and RNA from malignant cells; and DNA and RNA from mutated cells.

Examples of suitable natural soluble macromolecules for detection hereby include: chemokines, cytokines, growth factors, hormones, and proteins from normal and abnormal cells.

The principles of the invention may be illustrated by the following assay for detecting the presence of bacteria in a clinical specimen. In this illustration the germinogenic enzyme is alkaline phosphatase (EC 3.1.3.1), an ubiquitous enzyme in bacteria. An assay mixture consisting of a buffer solution with the following additions: (A) Adenosine 5'-monophosphate (AMP), a germinogenic substrate of alkaline phosphatase which will release the germinant adenosine upon enzymatic hydrolysis; and (B) microbial spores which are virtually devoid of alkaline phosphatase, but are capable of de novo synthesis of alkaline phosphatase during spore germination.

Under standard pH and temperature conditions (usually pH 7.2 and 37° C., respectively), bacterial cells which contain alkaline phosphatase will initiate within 5–20 minutes a self-sustained, analyte-independent cascade reaction because of the following interconnected events. First, if there is alkaline phosphatase in a test bacterium, the phosphatase will hydrolyze the AMP generating adenosine. Second, the adenosine will induce spore germination. Third, the spore germination will promote gene expression and accompanying de novo synthesis of alkaline phosphatase. Fourth, the de novo synthesized alkaline phosphatase will hydrolyze AMP producing more germinant which in turn will induce further rounds of spore germination generating de novo more alkaline phosphatase. This reaction sequence is an analyte-independent cascade because after the first two analyte dependent events (i.e. AMP hydrolysis and induction of spore germination) the system independently continues to produce germinant and concomitant spore germination.

In this particular example, the assay mixture is relatively simple since the germinogenic source, AMP, directly yields the germinant adenosine. In other embodiments of the invention, the assay mixture may contain enzymes that generate the germinant through a set of molecular reactions.

In still other embodiments of the invention the germinogenic enzyme present in the analyte will differ from the enzyme synthesized de novo during germination. Moreover, in still further embodiments, a different enzyme may be included in the assay mixture to generate the germinant through a combination of reactions.

When the analyte does not contain an intrinsic germinogenic enzyme, the analyte must be: (a) specifically immobilized on discrete microscopic particles (e.g., polystyrene beads or iron oxide particles) and (b) labeled with a germinogenic enzyme. Enzyme labeling may be either specific or nonspecific. Analyte immobilization and enzyme labeling are accomplished using conventional crosslinking reagents that react with macromolecules. For example, DNA analytes can be specifically immobilized on polystyrene beads coated with one or more sets of oligonucleotides containing sequences complementary to those of the DNA. For specific immobilization of proteins, the beads may be coated with antibodies specific for epitope(s) present in the analyte. Similar procedures may be used for specific enzyme labeling. For example, a DNA analyte can be specifically labeled using complementary oligonucleotides linked to a germinogenic enzyme by biotin-avidin bonds. Since each of these techniques is well known in the art further details may be readily found in the literature and thus are not included here.

Alternatively, the analyte can be immobilized on the wells of a plate such as a 96-well plate.

For analytes, such as viruses or bacteria, release of the nucleic acids or permeabilization of the organisms may be performed and this invention used to detect the released or permeabilized products.

The extent of the cascade produced can be assessed using any standard methodology for measuring spore germination or germination products. For example, germination may be measured by loss of spore birefringence which causes a reduction of optical density. Alternatively, the increase in redox potential due to de novo synthesis of oxidoreductive enzymes during germination may be measured by incorporating a redox indicator, such as resazurin, in the reaction mixture.

In another example, the increase in de novo synthesized β-D-galactosidase may be measured by incorporating a fluorogenic substrate, such as fluorescein di-β-D-galactoside, in the reaction mixture. Alternatively, the increase in esterase activity due to permeabilitization of the spores during germination may be measured by incorporating fluorescein diactetate in the reaction mixture.

An important feature of the invention is that assays can be set up in a billion-fold range of reaction-volumes extending from milliliters to picoliters ($10^{-12}$ liter). Thus, the invention may exploit the inverse relationship between assay-volume and assay-sensitivity. The enormous amplification power obtained by reducing the test-volume to picoliters is well recognized, and it is best exemplified by fluorogenic assays of β-galactosidase which have been extended to measurements of single enzyme molecules by reducing the test volume to 4.4 picoliters (Rotman, Measurements of single molecules of antibody by their ability to activate a defective enzyme. In: T.&. Sernetz (ed.) Berlin: Springer-Verlag, p. 333–337, 1973). As shown below, operating the system in the picoliter range allows for rapid analysis of individual bacterial cells.

For assay-volumes in the picoliter range, a particularly suitable disposable biosensor is shown schematically in FIG. 1. The biosensor 10 consists of a mesh 12 (25 mm diameter, made from commercially available nylon screen cloth) bonded to a nitrocellulose or other microporous membrane filter 14, having about 0.2 micron pores 15 to form a matrix with about 100,000 microwells 16 of about 5 picoliters each. Mounted on a conventional 25 mm filter holder (not shown in FIG. 1), the biosensor operates as a flowthrough device when mild pressure or vacuum is applied using, for example, a standard syringe.

In operation, a liquid suspension is formed by combining a sample containing a suspected analyte, a germinogenic source, and suitable spores. The suspension 18 is distributed, preferably uniformly, across the face of the nylon mesh. A vacuum is applied and the biosensor is incubated for a suitable period of time for spore germination to occur. Generally the time is about 15–60 minutes.

This biosensor is particularly suitable for highly sensitive, automated operations because it allows for multiple parallel assays which can be monitored as spatially distributed biochemical events using standard imaging hardware and software for computerized data acquisition and processing. For example, a device such as the Loats imaging system can be used as an imaging readout for the biosensor. Biosensors with microwells of different volumes can be easily constructed by using nylon (or other material) screens of different mesh sizes.

The operation of the biosensor is illustrated by an embodiment for detecting bacteria producing L-alanine dehydrogenase, an enzyme commonly used as an identification marker of some bacterial species including *Escherichia coli*. The enzyme generates L-alanine, a specific germinant for some microbial spores including *Bacillus subtilis* spores, according to the following reaction in which NADH (reduced nicotinamide adenine dinucleotide) is oxidized to NAD while ammonia is incorporated into pyruvic acid producing L-alanine:

(1)

L-Alanine dehydrogenase

Pyruvic acid + NH$_3$ + NADH ⟶ ...... ⟶ L-Alanine + NAD + H$_2$O

Parenthetically, the name of this enzyme is misleading because it is based on the reverse of reaction. The enzyme, however, may be used herein because it has three times more affinity for pyruvate than for L-alanine. The embodiment entails: (1) adding a test sample to genetically-modified *B. subtilis* spores suspended in buffer containing sodium pyruvate, ammonium sulfate, sodium lactate, and NADH. These spores synthesize de novo L-alanine dehydrogenase, and are genetically-modified to synthesize de novo lux enzymes producing bioluminescence (Cook, N. et al. Construction and detection of bioluminescent strains of *Bacillus subtilis*. J. Appl. Bacteriol. 75: 350–359, 1993); (2) passing the mixture through the biosensor, and incubating the biosensor for a time sufficient to allow for L-alanine production, spore germination and appearance of measurable bioluminescence in discrete microwells of the biosensor; and (3) imaging the biosensor, collecting, and processing the image data.

The embodiment provides not only an assay for bacterial detection and identification, but also as a quantitative measurement of the number of the bacteria in the sample. For example, if a 10 μL sample containing 500 bacteria per mL is tested, 5 of the 100,000 microwells of the biosensor will receive one bacterium each and a bioluminescent image will then show 5 illuminated microwells randomly distributed over the biosensor. In contrast, a 10 μL sample containing 50,000 bacteria per mL will show 500 illuminated microwells. Using Poisson's distribution probability, the number of bacteria in the sample can be calculated from the total number of illuminated microwells in the image.

Because the biosensor's response to bacteria is measured as a number of illuminated microwells, and not by any intensity of bioluminescence, the assay has a linear response to bacterial number independent of the amount of germinogenic enzyme present in the tested bacteria. The dynamic range of the assay extends from zero to about $10^7$ bacteria per mL (for 10 μL samples), a range suitable for most practical applications. The probability of a microwell having two or more bacterial cells is negligible unless there is cellular aggregation. For example, for a 10 μL sample containing $10^6$ bacteria per mL, the probability of a microwell having 2 or more bacteria is less than 0.6%.

Many of the embodiments of the present invention employ optical detection of spore germination. Detection can be enhanced through the use of spores producing colored, fluorescent or phosphorescent enzymatic products during germination. In a preferred embodiment employing the biosensor depicted in FIG. 1, a charge-coupled device (CCD) readout is used to image the response of the system to the analyte in the form of discrete luminescent microwells randomly distributed throughout the biosensor.

The components and reagents of the assay system of the present invention may be supplied (in aqueous or lyophilized form) in the form of a kit in which the simplicity and sensitivity of the assay are preserved. All necessary reagents can be added in excess to accelerate the reactions. In a preferred embodiment, the kit will also comprise a preformed biosensor designed to receive a sample containing an analyte. The exact components of the kit will depend on the type of assay to be performed and the properties of the analyte being tested.

Another important feature of the invention is that the analyte-independent cascade reaction promotes de novo synthesis or activation of reporter enzymes suitable for monitoring the system. In a preferred embodiment, the spore-forming bacteria is a *B. subtilis* strain 3610 VIN, which has been genetically-modified to carry chromosomal lux bioluminescence genes (Cook, N. et al, Construction and detection of bioluminescent strains of *Bacillus subtilis.*, J. Appl. Bacteriol. 75:350–359, 1993). The spores of this strain do not exhibit bioluminescence. Rather, they become bioluminescent during germination. In another preferred embodiment, the spores are from *B. subtilis* genetically-modified to carry chromosomal lac genes producing β-D-galactopyranoside as the reporter enzyme which can be measured by a variety of sensitive standard assays. Alternatively, in a preferred embodiment, the spores from *B. subtilis* are genetically-modified to carry a chromosomal gene coding for a green fluorescent protein which serves as reporter molecule because of its strong and specific fluorescence.

Bacterial spores may be obtained by growing bacteria in sporulation agar medium for four days. The spores are harvested in a convention manner, e.g. with distilled water. Thereafter, they are processed, e.g. heated at 65° C. for 30 min, to kill vegetative cells and to inactivate enzymes present and washed several times with distilled water. The heating-and-washing process is repeated and the spores are resuspended in distilled water. Spore suspensions have given satisfactory results after storage at 4° C. for up to six months. Alternatively, the spores may be lyophilized for storage. Spore preparations with detectable background of enzymatic activity may be re-heated at 65° C. to lower the background.

In some embodiments, permeabilization or lytic agents to facilitate access of germinogenic substrates to intracellular enzymes in the analyte or liberate nucleic acids and other macromolecules may be present. Usually, such agents do not affect enzymatic activity. Examples of permeabilization agents disrupting the outer membrane of some gram-negative bacteria include mild detergents, such as Triton® X-100, and cationic polypeptides, such as polymyxin B sulfate.

Many of the embodiments of the present invention employ optical detection of spore germination. Detection can be enhanced through the use of spores producing colored, fluorescent or phosphorescent enzymatic products during germination. In a preferred embodiment employing the biosensor depicted in FIG. 1, a charge-coupled device (CCD) readout is used to image the response of the system to the analyte in the form of discrete luminescent microwells randomly distributed throughout the biosensor.

Another preferred embodiment is to entrap the analyte within individual emulsified droplets containing buffer, about 10 to 500 spores, a germinogenic source, and an early indicator of spore germination.

In the following non-limiting examples, all parts and percents are by weight unless otherwise specified.

EXAMPLE 1

Detection of *E. coli* Producing β-Lactamase II (Cephalosporinase)

Detection of bacteria containing β-lactamases (EC 3.5.2.6) is clinically important because the enzymes are usually good markers of resistance to β-lactam antibiotics. Spores derived from *B. cereus* 569H (ATCC 27522), a strain with constitutive β-lactamase II, are used. The spores germinate in a mixture of L-alanine and adenosine.

In this example, spores are employed which synthesize de novo β-lactamase II, an enzyme which produces L-alanine (the germinant) by fragmentation of L-alanine cephalosporin according to the following reaction (2):

(2)

β-lactamase II

L-alanine cephalosporin + $H_2O$ ⟶ .... ⟶ L-alanine + cephalosporoate

The assays are set up in 96-well plates. Each well receives 0.18 mL of spores ($5 \times 10^8$ spores per mL) suspended in phosphate buffer (0.1 M, pH 7.2) containing 2 mM adenosine and 50 mM L-alanine cephalosporin, the germinogenic substrate. This substrate is a C3' alanine-substituted cephalosporin liberating L-alanine upon enzymatic hydrolysis of the β-lactam ring according to reaction (2).

Test samples (20 μL) containing *E. coli* K-12 (ATCC 15153) cells suspended in distilled water are dispensed into the wells and the plate is incubated at 37° C. The number of cells in each test sample varies from 50 to 1,000. Appropriate positive and negative controls are included in the assay.

Using a microtiter plate spectrophotometer with printed read-out (BIO-TEK Instruments, Inc.), the optical density (at 490 nm) of individual wells is recorded at zero time and at 15 min intervals. Under these conditions, *E. coli* cells trigger a cascade reaction because of the following interconnected reactions: (1) *E. coli* β-lactamase II hydrolyses L-alanine cephalosporin liberating L-alanine which induces germination in spores near the *E. coli* cells and (2) spore germination promotes de novo synthesis of β-lactamase II which initiates an analyte-independent cascade of spore germination that propagates throughout the reaction mixture. The course of the cascade reaction is measured by a reduction in optical density due to loss of spore birefringence during germination.

The system responds to the presence of about 120 β-lactamase-producing bacteria by exhibiting a 40% loss of optical density after 15 min incubation at 37° C. The optical density loss reaches a 53% plateau after 30 min.

EXAMPLE 2

Detection of Indole-producing *E. coli* by Combining Two Enzymes

Identification of bacteria producing tryptophanase (EC 4.1.99.1) is clinically important because the ability to synthesize tryptophanase correlates well with bacterial ability to grow in the intestine of animals and humans. Bacterial tryptophanase is measured by the production of indole which is used in the clinic as an identification marker for Enterobacteriaceae and Pasteurella.

Spores derived from *B. subtilis* VIN (NCTC 3610), a genetically-engineered strain with chromosomal lux genes for bioluminescense, are prepared. The spores are not bioluminescent but become so during germination. The spores require L-alanine for germination.

In this example, the analyte is *E. coli* K-12 (ATCC 15153) cells producing tryptophanase, an enzyme which catalyzes the reaction:

(3)

Tryptophanase

L-Tryptophan + H₂O ⟶ .......... ⟶ Pyruvate + Inndole + NH₃

The direct reaction product pyruvate is then converted to L-alanine, the germinant, by the presence of glutamic-pyruvic transaminase in the assay mixture. This enzyme catalyzes the reaction:

(4)

Glutamic-Pyruvic Transaminase

Pyruvate + L-Glutamate ⟶ ..... ⟶ L-Alanine + α-Ketoglutarate

Test samples of 20 µL each containing variable numbers of E. coli cells suspended in distilled water are mixed with 100 µL of spores (2×10⁹ spores per mL) suspended in Tris/HCl buffer (20 mM, pH 7.2) containing 20 mM L-tryptophan, 20 mM potassium L-glutamate, and 0.1 units of glutamic-pyruvic transaminase (EC 2.6.1.2, Sigma Chemicals, St. Louis, Mo.). Without delay, the mixture is introduced on the disposable biosensor depicted in FIG. 1 mounted on a conventional Millipore filtration apparatus. The reaction mixture is forced into the biosensor using gentle suction with a 2-ml syringe, and the biosensor is incubated in a humidified chamber for 30–90 minutes. Since the biosensor has about 100,000 microwells, each microwell will receive about 2,000 spores while individual bacterial cells present in the sample will distribute randomly among the microwells.

In this example, E. coli cells, the analyte, produce an analyte-independent cascade reaction because of the following interconnected events: (1) E. coli tryptophanase converts the L-tryptophan in the reaction mixture to indole and pyruvate; (2) in the presence of L-glutamate and glutamic-pyruvic transaminase, the pyruvate produced by the analyte is converted to L-alanine which induces spore germination with concomitant de novo synthesis of tryptophanase; and (3) the de novo synthesized tryptophanase inites an analyte-independent cascade in which additional tryptophanase is produced as well as bioluminescence enzymes coded by the lux genes.

The response of the system as a function of time is measured by the number of microwells with measurable bioluminescence, and the light intensity of individual microwells.

Bioluminescence is measured using a microscope equipped with a light detector. The data are converted to number of E. coli cells per mL of sample, and relative amount of tryptophanase per cell.

CCD imaging is used to capture a bioluminescent image of the entire biosensor. This type of detection allows for parallel assays, quantitative imaging of spatially distributed events, and computerized data acquisition and processing. The dynamic range of the system extends from 0 to 100,000 bacterial cells per 20 µL sample.

EXAMPLE 3

ELISA for Cytokines

In this example, the invention is applied to a conventional two-site (sandwich) ELISA (enzyme-linked immunosorbent assay) for cytokines using TNF-α as the analyte. Immunological reagents, L-alanine dehydrogenase (EC 1.4.1.1), and other chemicals are from Sigma Chemicals (St. Louis, Mo.). Spores are derived from B. subtilis 168 (ATCC 27370), a strain producing L-alanine dehydrogenase. The spores require L-alanine for germination.

The de novo synthesized enzyme initiating the analyte-independent cascade reaction is L-alanine dehydrogenase which produces the germinant L-alanine according to reaction (1) shown above.

Reaction mixture. Assays are set up in 96-well plates previously coated with anti-TNF-α immunoglobulin from goat antiserum and blocked with bovine serum albumin (BSA). The plates are stored at 4° C. for up to 4 weeks. Test samples, controls, and recombinant TNF-α standards are dispensed into designated wells, and the plate is sealed, incubated at 37° C. for 30 minutes, emptied, and rinsed once with phosphate buffered saline containing 1% BSA (PBS-BSA). Monoclonal antibody (mAb) to TNF-α is dispensed into each well, the plate is sealed, incubated at 37° C. for 30 minutes, emptied, and rinsed twice with PBS-BSA. A covalent conjugate consisting of L-alanine dehydrogenase and anti-mouse IgG immunoglobulin from goat antiserum is dispensed into each well. The plate is sealed, incubated at 37° C. for 30 minutes, emptied, and rinsed four times with PBS-BSA. At this stage the system is set up by dispensing into each well 0.18 mL of spores (5×10⁸ spores per mL) suspended in Tris/HCl buffer (20 mM, pH 7.5) containing 20 mM sodium pyruvate, 40 mM ammonium sulfate, and 20 mM NADH. Optical density readings are recorded at zero time and at 15-min intervals as indicated above for Example 1. A loss of optical density indicates presence of TNF-α in the sample.

In this example, TNF-α is detected because the L-alanine dehydrogenase-antibody conjugate binds specifically to the analyte immobilized in the well and generates L-alanine which induces spore germination in the vicinity of the analyte. Spore germination results in de novo synthesis of L-alanine dehydrogenase which initiates an analyte-independant cascade reaction in which further germination produces more L-alanine dehydrogenase which in turn generates more L-alanine and more germination. Typically, samples with about 60 fentograms of TNF-α per ml will produce a 40% loss of optical density after 60–120 min of incubation.

EXAMPLE 4

Detection of Urease-Producing Bacteria

Bacteria with enzymes whose products affect pH may also be analyzed. An example of clinical importance is urease, an enzyme which has been used for bacterial identification since 1941. Bacterial urease activity is conventionally measured by an increase in the pH of the growth medium due to formation of ammonium carbonate.

Spores derived from Bacillus pasteurii (ATCC 11859), a strain producing urease, are prepared as indicated above. The spores require L-alanine for germination.

In this example, the analyte is Helicobacter pilori (ATCC 43504) cells which produce urease, an enzyme catalyzing the reactions:

Urease

(5)

Assays are set up in 96-well plates. Each well receives 0.18 mL of spores ($5\times10^8$ spores per mL) suspended in low ionic phosphate buffer (0.005 M, pH 3.0) containing 50 mM urea, 0.5 mM L-alanine, and fluorescein as pH indicator.

Test samples (20 μL) containing *H. pilori* cells suspended in low ionic phosphate buffer pH 3.0 are dispensed into wells and the plate is incubated at 37° C. The total number of cells in each test sample varies from 50 to 5,000. Appropriate positive and negative controls are included in the assay. Under these conditions, spores do not germinate because of low pH, but in wells with bacteria producing urease the pH will rise to normal values. At normal pH, the L-alanine in the reaction mixture will induce spore germination. *H. pilori* cells trigger an analyte-independent cascade reaction because of the following interconnected reactions: (1) *H. pilori* cells, the analyte, hydrolyse urea liberating ammonia which elevates the pH of the reaction mixture in the vicinity of the analyte allowing nearby spores to be induced by L-alanine to germinate; and (2) spore germination promotes de novo synthesis of urease which hydrolyzes urea raising the pH of the reaction mixture and causing a cascade of spore germination.

The course of the cascade reaction is measured fluorimetrically by the change in pH due to spore germination using fluorescein as pH indicator.

EXAMPLE 5

Detection of Bacteria Producing Phosphatases

The invention is used to detect bacteria producing phosphatases, a family of ubiquitous enzymes in bacteria. More specifically, the invention is used to detect bacterial contaminations in body fluids, water, food products and others as follows. Spores derived from *B. cereus* (ATCC 27348), a strain producing phosphatases, are used. The spores require a mixture of L-alanine and adenosine for germination.

In this example, the analyte is *E. coli* K-12 (ATCC 15153) cells which produce different phosphatases which catalyze the following reaction:

Phosphatases

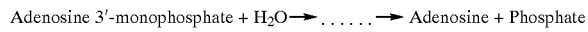

(7)

Assays are set up in 96-well plates. Each well receives 0.18 mL of spores ($5\times10^8$ spores per mL) suspended in Tris/HCl buffer (20 mM, pH 7.8) containing 0.5 mM L-alanine and 10 mM adenosine 3'-monophosphate, the germinogenic substrate.

Test samples (20 μL) containing *E. coli* cells suspended in water are dispensed into the wells and the plate is incubated at 37° C. The number of cells in each test sample varies from 50 to 1,000. Appropriate positive and negative controls are included in the assay.

The response of the system is measured by loss of optical density as indicated above for Example 1. In this example, *E. coli* cells are detected because of the following interconnected reactions: (1) *E. coli* phosphatases hydrolyse adenosine 3'-monophosphate liberating adenosine which induces germination in spores near the *E. coli* cells and (2) spore germination promotes de novo synthesis of phosphatases which initiate an analyte-independent cascade of spore germination that propagates throughout the reaction mixture. The course of the cascade reaction is measured by reduction in optical density due to loss of spore birefringence during germination.

EXAMPLE 6

Detection of Viral RNA

In this example, the invention is used to detect viral RNA present in a clinical sample. The RNA is captured on small, spherical polystyrene beads coated with single-stranded oligonucleotides complementary to the analyte, and a germinogenic enzyme is specifically attached to the immobilized analyte using single-stranded oligonucleotide linkers that are complementary to the analyte. After separating and washing the beads to remove unbound reagents, the beads are mixed with spores and a germinogenic source, and the mixture is introduced in the biosensor as described above in Example 2.

As in Example 2, the spores are derived from *B. subtilis* VIN (NCTC 3610), a genetically-engineered strain with chromosomal lux genes for bioluminescence. The spores require L-alanine for germination.

The germinogenic enzyme is L-alanine dehydrogenase (EC 1.4.1.1) producing L-alanine, the germinant, according to reaction (1) above.

Target viral RNA is released from the virus using detergents and degradative enzymes, dissociated into single-strands, hybridized with biotin-labeled complementary oligonucleotides, and then mixed with an appropriate number (e.g., $10^5$–$10^7$ per mL) of monodisperse polystyrene beads (2–5 μm diameter) coated with complementary single-stranded oligonucleotides. After 30–60 minutes of incubation at room temperature to allow for RNA binding to the beads, the beads are separated by centrifugation, washed, resuspended in buffer containing a covalent conjugate of avidin and L-alanine dehydrogenase, and incubated for 30–60 minutes at room temperature to allow for binding of the conjugate to the target RNA immobilized on the beads via avidin-biotin coupling. After incubation, the beads are separated, washed, resuspended in 100 μL of the reaction mixture and without delay introduced in the biosensor as indicated above for Example 2.

The mixture consists of 100 μL of spores ($2\times10^9$ spores per mL) suspended in Tris/HCl buffer (20 mM, pH 7.5) containing 20 mM sodium pyruvate, 40 mM ammonium sulfate, and 20 mM NADH.

In this example, the microwells of the biosensor which will have about 2,000 spores each, and individual beads with bound target RNA will distribute at random in the microwells. In microwells with a bead containing immobilized target RNA, the RNA-bound L-alanine dehydrogenase will generate L-alanine from pyruvate, ammonia and NADH. The L-alanine will initiate an analyte-independant cascade reaction as indicated above for Example 3. The end point of the reaction is a bioluminescence image of the biosensor which is captured using a CCD video camera. The dynamic range of the system extends from 0 to 100,000 copies of viral RNA per tested sample.

EXAMPLE 7

Detection of L-Alanine Aminopeptidase Producing Bacteria Using Two Different Germinogenic Substrates A clinically important enzymatic marker for classification and identification of pathogenic bacteria is L-alanine aminopeptidase because the enzyme is present in significant amounts in Gram-negative bacteria but not in Gram-positives. In this example, E. coli K-12 (ATCC 15153) cells are identified using two different germinogenic sources.

Spores are derived from B. subtilis 168 (ATCC 27370), a strain producing L-alanine dehydrogenase. The spores require L-alanine for germination.

The E. coli cells (the analyte) produce L-alanine aminopeptidase which produces L-alanine (the germinant) according to the following reaction:

(6)

L-alanine aminopeptidase

L-alanine-p-nitroanilide + H$_2$O ⟶ ... ⟶ L-alanine + p-nitroaniline

The de novo synthesized enzyme initiating the analyte-independent cascade reaction is L-alanine dehydrogenase (EC 1.4.1.1) which produces the germinant L-alanine according to reaction (1) shown above.

Assays are set up in 96-well plates. Each well receives 0.18 mL of spores ($5\times10^8$ spores per mL) suspended in Tris-HCl buffer (20 mM, pH 7.2) containing 20 mM L-alanine-p-nitroanilide hydrochloride, 20 mM sodium pyruvate, 40 mM ammonium sulfate, and 20 mM NADH.

Test samples (20 μL) containing E. coli cells suspended in distilled water are dispensed into the wells and the plate is incubated at 37° C. The number of cells in each test sample varies from 50 to 1,000. Appropriate positive and negative controls are included in the assay. Optical density readings are recorded at zero time and at 15 minute intervals as indicated above for Example 1. A loss of optical density indicates presence of bacterial L-alanine aminopeptidase in the sample.

In this example, E. coli cells are detected because of the following interconnected reactions: (1) the E. coli L-alanine aminopeptidase hydrolyses L-alanine-p-nitroanilide liberating L-alanine which will induce germination in spores near the E. coli cells and (2) spore germination promotes de novo synthesis of L-alanine dehydrogenase which will generate L-alanine from pyruvate, ammonia and NADH thus initiating an analyte-independant cascade reaction as indicated above for Example 3.

EXAMPLE 8

Detection of Bacteria in Emulsified Droplets Containing Spores

In this example, the invention is used to detect bacteria producing phosphatases. The spores, germinogenic substrate, and enzymatic production of germinant are identical to those described above for Example 5.

Assays are set up in standard glass tubes. For testing, about $3\times10^8$ spores are suspended in one mL Tris/NaCl buffer (20 mM Tris, 50 mM NaCL, pH 7.4) containing 1.0 mM L-alanine and 10 mM adenosine 5'-monophosphate, the germinogenic substrate. Test samples (20 μL) containing E. coli cells suspended in water are added to the spore suspension followed immediately by 5 μL of fluorescein diacetate solution (12 mM in dimethyl sulfoxide). The number of cells in each test sample varies from 1 to 1,000. The suspension is gently shaken for 20–30 seconds until visible aggregates are formed. At this stage, about one mL of mineral oil is dispensed into the tube, and the tube is shaken for another 10–20 seconds. Under these conditions, the spores together with the target bacteria are found entrapped in microscopic droplets dispersed in the mineral oil. Droplet diameter ranges from 5 to 50 microns. Appropriate positive and negative controls are included in the assay.

Spore germination is measured by appearance of acetylesterase activity which is quantitatively measured by hydrolysis of fluorescein diacetate, a specific fluorogenic substrate. The acetylesterase is not detectable in the spores before the onset of germination. Enzyme activity appears within 5–10 minutes after exposing the spores to germinant(s). The target cells of E. coli are detected because of the following interconnected reactions which occur within individual droplets:

(1) E. coli phosphatases hydrolyse adenosine 5'-monophosphate liberating adenosine which induces germination in spores near the E. coli cell;

(2) spore germination promotes de novo synthesis of phosphatases which initiate an analyte-independent cascade of spore germination that propagates throughout the spores in the microdroplet;

(3) the course of the cascade reaction is measured by hydrolysis of fluorescein diacetate which occurs exclusively in germinating spores (The hydrolysis product, fluorescein, is highly fluorescent and remains inside the microdroplet.); and (4) The response of the system as a function of time is measured by the number of fluorescent droplets of a selected diameter and by the fluorescent light intensity of individual droplets.

The fluorescent light emitted by microdroplets may be measured quantitatively using a fluorescence microscope equipped with a light detector. The data are converted to number of target cells per mL of sample, and relative amount of phosphatase per target cell.

In a preferred embodiment, a large number of microdroplets transfered are deposited in a microscope chamber filled with mineral oil. As described above for Example 2, a CCD camera is used to capture fluorescence images of the entire chamber at time intervals. This type of detection allows for parallel assays, quantitative imaging of spatially distributed events, and computerized data acquisition and processing.

What is claimed is:

1. A method for detecting the presence of a particulate analyte in a test sample which comprises the steps of:

(1) combining a test sample containing the particulate analyte with a reaction mixture comprising (i) microbial spores that sense an analyte-specific signal and respond to that signal by establishing an analyte-independent signal amplification system and (ii) a germinogenic source, (2) incubating said mixture for a time sufficient to allow for enzymatic conversion of the germinogenic source to a germinant and spore germination by a propagating cascade of spore germination generated through de novo synthesized enzymes;

(3) detecting spore germination by a measurable parameter; and (4) correlating the presence of the particulate analyte in the test sample by the detecting of spore germination;

wherein the target analyte generates the germinant by enzymatic action on the germinogenic source and wherein the target analyte is initially incapable of generating the germinant by enzymatic action on the germinogenic source but is made capable of so doing during the analysis.

2. The method of claim 1, wherein the target analyte is initially incapable of generating a germinant and is made capable of generating a germinant by means of a germinogenic enzyme attached to the analyte.

3. The method of claim 1, wherein the analyte is labeled with a germinogenic enzyme to generate an enzyme which results in the enzymatic conversion of the germinogenic source to germinant.

4. The method of claim 3, wherein the enzyme labeling is specific.

5. The method of claim 4, wherein a DNA analyte is specifically labeled using complementary oligonucleotides linked to a germinogenic enzyme by biotin-avidin bonds.

6. The method of claim 1, wherein prior to the combining the spores are processed so as to be devoid of active germinant.

7. The method of claim 6, wherein the spores are processed by heating and washing with water.

8. The method of claim 1, wherein the detection is made by loss of spore birefringence.

9. The method of claim 1, wherein the detection is made by the appearance of enzymatic activity due to an enzyme which is synthesized de novo in the germinating spores.

10. The method of claim 9, wherein the enzyme synthesized de novo is an oxidoreductive enzyme and a redox indicator is added to the reaction mixture.

11. A method for detecting the presence of an analyte in a test sample which comprises the steps of:

(1) combining a test sample containing the analyte with a reaction mixture comprising (i) microbial spores that sense an analyte-specific signal and respond to that signal by establishing an analyte-independent signal amplification system, (ii) a germinogenic source, and (iii) a fluorogenic material;

(2) incubating said mixture for a time sufficient to allow for enzymatic conversion of the germinogenic source to a germinant and for spore germination; and (3) detecting spore germination by the appearance of enzymatic activity due to a fluorogenic enzyme which is synthesized de novo in the germinating spores;

(4) correlating the presence of the particulate analyte in the test sample by the detecting of spore germination;

wherein the target analyte generates the germinant by enzymatic action on the germinogenic source and wherein the target analyte is initially incapable of generating the germinant by enzymatic action on the germinogenic source but is made capable of so doing during the analysis.

* * * * *